United States Patent
Li et al.

(10) Patent No.: US 11,504,052 B2
(45) Date of Patent: Nov. 22, 2022

(54) MODELING METHOD FOR SCREENING SURGICAL PATIENTS

(71) Applicants: TSINGHUA UNIVERSITY, Beijing (CN); BEIJING PINS MEDICAL CO., LTD, Beijing (CN)

(72) Inventors: Luming Li, Beijing (CN); Hongyun Liu, Beijing (CN); Zhao Yang, Beijing (CN)

(73) Assignee: BEIJING PINS MEDICAL CO., LTD., Beijing (CN)

( * ) Notice: Subject to any disclaimer, the term of this patent is extended or adjusted under 35 U.S.C. 154(b) by 524 days.

(21) Appl. No.: 16/086,428

(22) PCT Filed: Aug. 4, 2017

(86) PCT No.: PCT/CN2017/095951
§ 371 (c)(1),
(2) Date: Sep. 19, 2018

(87) PCT Pub. No.: WO2018/036367
PCT Pub. Date: Mar. 1, 2008

(65) Prior Publication Data
US 2019/0090803 A1 Mar. 28, 2019

(30) Foreign Application Priority Data

Aug. 23, 2016 (CN) .......................... 201610708479.3

(51) Int. Cl.
*A61B 5/00* (2006.01)
*A61B 5/0245* (2006.01)
(Continued)

(52) U.S. Cl.
CPC .......... *A61B 5/4094* (2013.01); *A61B 5/0245* (2013.01); *A61B 5/02405* (2013.01);
(Continued)

(58) Field of Classification Search
CPC ..... A61B 5/4094; A61B 5/349; A61B 5/7278; A61B 5/02405; A61B 5/0245;
(Continued)

(56) References Cited

U.S. PATENT DOCUMENTS

| | | | | |
|---|---|---|---|---|
| 2014/0221780 A1* | 8/2014 | Goldberger | .......... | A61B 5/0476 600/301 |
| 2015/0223759 A1* | 8/2015 | Ong | ..................... | A61B 5/0205 600/301 |

(Continued)

FOREIGN PATENT DOCUMENTS

| | | |
|---|---|---|
| CN | 106264510 A | 1/2017 |
| CN | 106343992 A | 1/2017 |
| CN | 106551691 A | 4/2017 |

OTHER PUBLICATIONS

Goldberger et al.—Title: "Multiscale entropy analysis of biological signals" (URL: https://arxiv.org/abs/physics/0604040 ) (Year: 2005).*

(Continued)

*Primary Examiner* — Alexander Satanovsky
(74) *Attorney, Agent, or Firm* — Grossman, Tucker, Perreault & Pfleger, PLLC

(57) ABSTRACT

A modeling method for screening surgical patients, used in analysis modeling for heart rate variability (HRV). Low-cost, portable and wearable signal acquisition equipment is utilized to acquire an electrocardiography (ECG) signal of an epileptic 24 hours before surgery; a multiscale entropy (MSE) of the ECG is calculated by means of a programmed HRV analysis method, wherein characteristic parameters representing heart rate complexity are extracted on the basis of an MSE curve, and a medical refractory epileptic suitable for vagus nerve stimulation (VNS) surgery is accurately and efficiently screened, thus avoiding unnecessary expenditures and avoiding delaying an optimal opportunity for treatment. Meanwhile, the curative effects of the VNS treatment may (Continued)

be wholly improved by means of clearly selecting VNS surgical indication patients according to the characteristic parameters of the MSE complexity of the ECG.

5 Claims, 6 Drawing Sheets

(51) Int. Cl.
| | | |
|---|---|---|
| *G16H 50/50* | (2018.01) | |
| *G16H 40/63* | (2018.01) | |
| *G06Q 50/22* | (2018.01) | |
| *G16H 50/30* | (2018.01) | |
| *G06Q 10/04* | (2012.01) | |
| *G16H 50/20* | (2018.01) | |
| *A61B 5/349* | (2021.01) | |
| *A61B 5/024* | (2006.01) | |
| *A61B 5/316* | (2021.01) | |
| *A61B 5/339* | (2021.01) | |
| *A61B 5/341* | (2021.01) | |
| *A61B 5/369* | (2021.01) | |

(52) U.S. Cl.
CPC ............ *A61B 5/349* (2021.01); *A61B 5/7278* (2013.01); *G06Q 10/04* (2013.01); *G06Q 50/22* (2013.01); *G16H 40/63* (2018.01); *G16H 50/20* (2018.01); *G16H 50/30* (2018.01); *G16H 50/50* (2018.01); *A61B 5/316* (2021.01); *A61B 5/339* (2021.01); *A61B 5/341* (2021.01); *A61B 5/369* (2021.01); *A61B 5/4035* (2013.01); *A61B 2505/05* (2013.01)

(58) Field of Classification Search
CPC ......... A61B 5/316; A61B 5/339; A61B 5/341; A61B 5/369; A61B 2505/05; A61B 5/4035; A61B 5/6802; A61B 5/7282; A61B 5/318; G16H 50/50; G16H 40/63; G16H 50/30; G16H 50/20; G06Q 50/22; G06Q 10/04
See application file for complete search history.

(56) References Cited

U.S. PATENT DOCUMENTS

2015/0314128 A1* 11/2015 Talkachova .......... A61N 1/3627
607/17
2016/0113538 A1 4/2016 Chiu et al.

OTHER PUBLICATIONS

A Sarkar, P. Barat—Title: Multiscale Entropy Analysis: A New Method to Detect Determinism in a Time Series (Year: 2006).*
Ping-Huang Tsai et al.—Title: A Novel Application of Multiscale Entropy in Electroencephalography to Predict the Efficacy of Acetylcholinesterase Inhibitor in Alzheimer's Disease (Year: 2015).*
Timoth'ee Cour et al. "Spectral Segmentation with Multiscale Graph Decomposition", Proceeding of 2005 IEEE Computer Society Conference on Computer Vision and Pattern Recognition (CVPR'05), 2005.*
Michael A. Busa et al. "Multiscale entropy: A tool for understanding the complexity of postural control", Journal of Sport and Health Science 5 (2016) 44-51.*
International Search Report dated Oct. 26, 2017 of corresponding International application No. PCT/CN2017/095951; 4 pgs.

* cited by examiner

MODELING METHOD FOR SCREENING SURGICAL PATIENTS

TECHNICAL FIELD

The invention relates to a modeling method for screening surgical patients, in particular to a modeling method for patients with Vagus Nerve Stimulation (VNS) indications.

BACKGROUND

Epilepsy as a disease affects the lives of patients. For most patients, epileptic seizures could be controlled by one or more drugs. However, some patients are still not sensitive to drug treatment. These patients are called patients with medical refractory epilepsy. As an adjuvant therapy, Vagus Nerve Stimulation (VNS) can effectively control epileptic seizures in patients with medical refractory epilepsy. However, the individual differences in efficacy thereof are very large and uncertainties are pretty high. Statistical analysis shown that, epileptic seizures were completely relieved in only 5% to 9% of patients with medical refractory epilepsy who were treated with VNS surgery, about 10% of patients were completely ineffective, and the rest shown seizure frequency reduction with varying degrees. Overall, 50% reduction in seizure frequencies could be achieved in 50%-60% of patients with medical refractory epilepsy who were treated with VNS surgery. In view of uncertainties and large individual differences in the efficacy of VNS for treating medical refractory epilepsy, researchers have been trying to screen patients suitable for VNS surgery through preoperative evaluation.

At present, there has been no definitive screening method for VNS surgical indications clinically applied. Meanwhile, studies on VNS efficacy factors have been performed based on EEG (Electroencephalography, EEG), Magnetic Resonance Imaging data (MRI), patient demographic characteristics (gender, age, etc.), clinical history (disease duration), seizure characteristics (including seizure type, seizure frequency, lesion location, etc.), and the conclusions thereof are not consistent, sometimes even contradictory.

The solution in the prior art is shown in FIG. 1. Firstly, systematic and comprehensive preoperative evaluations are performed for patients with medical refractory epilepsy (including demographic characteristics, medical history, seizure characteristics, MRI, EEG, etc.) before VNS surgery. Then, VNS implantation surgery is operated. After about 2 weeks, the devices are turned on. According to each patient's specific response to VNS acute stimulation, stimulation parameters are gradually adjusted in accordance with the VNS product performance and technical features, and seizure reduction of all patients are regularly analyzed. After the corresponding follow-up period (usually 1 year), the patients are classified according to reduction of seizures (i.e., efficacy). Finally, the preoperative evaluation data of patients with different efficacies are statistically analyzed, and parameters which are statistically different between patient groups are selected as sensitive factors for screening VNS patients or predicting efficacy.

The existing EEG and MRI methods have disadvantages of high cost, complicated operations, and high requirements on professional knowledge. Overall, studies based on these methods have not been clinically applied. The main reason lies in inconsistent or even contradictory conclusions for an identical problem. The method based on 24-hour dynamic ECG signals of the present invention only requires a subject to wear a portable dynamic ECG recording box, and the ECG data is collected without limiting the subject's activities, which is simple. 24-hour dynamic ECG is charged ¥240 yuan in ordinary hospital outpatients, which is relatively low, compared with long-term video electroencephalography and nuclear magnetic resonance imaging which are charged about ¥1,000 yuan. Most of all, compared with EEG and MRI, the 24-hour dynamic electrocardiogram acquisition is not limited by activities, thus is relatively simple and has good consistency.

Heart Rate Variability (HRV) refers to changes of adjacent cardiac intervals with time in Electrocardiography (ECG) signals. It originates from the autonomic nervous system's modulation of the sinus node's self-discipline, which leads to tens of milliseconds or even greater differences or fluctuations between inter-beat intervals. HRV contains a large amount of information about neurohumoral regulation, which is currently a quantitative, non-invasive and repeatable indicator for assessing activities and regulatory functions of the autonomic nervous system and the cardiovascular system. HRV analysis can indirectly reflect the interaction between sympathetic and parasympathetic nerves.

To date, there have been no studies and technical solutions for screening VNS patients using electrocardiographic signal HRV analysis technology. Epileptic diseases have a close relationship with cardiac autonomic dysfunction. With the onset and progression of epilepsy, a patient's cardiac autonomic nervous system balance is broken, which is generally manifested as increased sympathetic nerve activities and decreased parasympathetic nerve activities. Based on this conclusion, low-cost, portable and wearable signal acquisition equipment is adapted in the present invention, thus 24-hour ECG signals of an epileptic before surgery could be acquired. A multiscale entropy (MSE) of ECG could be calculated through a programmed HRV analysis, wherein characteristic parameters representing heart rate complexity are extracted on the basis of a MSE curve, thus a medical refractory epileptic suitable for VNS surgery could be accurately and efficiently screened.

SUMMARY OF THE INVENTION

The applicant found that epileptic diseases have a close relationship with cardiac autonomic dysfunction. With the onset and progression of epilepsy, a patient's cardiac autonomic nervous system balance is broken, which is generally manifested as increased sympathetic nerve activities and decreased Vagus nerve activities. Moreover, it is also found that Heart Rate Variability (HRV) is a very important indicator. HRV refers to changes of adjacent cardiac intervals with time in Electrocardiography (ECG) signals. It originates from the autonomic nervous system's modulation of the sinus node's self-discipline, which leads to tens of milliseconds or even greater differences or fluctuations between inter-beat intervals. HRV contains a large amount of information about neurohumoral regulation, which is currently a quantitative, non-invasive and repeatable indicator for assessing for assessing activities and regulatory functions of the autonomic nervous system and the cardiovascular system. HRV analysis can indirectly reflect the interaction between sympathetic and parasympathetic nerves.

Based on this finding, low-cost, portable and wearable signal acquisition equipment is adapted in the present invention, thus 24-hour ECG signals of an epileptic before surgery could be acquired. A multiscale entropy (MSE) of ECG could be calculated through a programmed HRV analysis, wherein characteristic parameters representing heart rate complexity are extracted on the basis of an MSE curve, and a medical refractory epileptic suitable for VNS surgery could be accurately and efficiently screened, thus saving unnecessary expenditures and avoiding delaying the optimal timing for treatment. At the same time, a patient suitable for VNS surgery is clearly selected through characteristic parameters of ECG's MSE heart rate complexity, which could generally improve the efficacy of VNS therapy.

The present invention provides a modeling method for screening surgical patients, wherein, modeling is based on heart rate variability.

Further, the method comprises the following steps:

1) collecting ECG data in vitro;

2) selecting sinus NN interval data;

3) performing MSE calculation on the selected sinus NN interval sequence;

4) extracting parameters representing heart rate complexity by means of a MSE curve.

The specific method of steps 3)-4) is as follows:

i. performing coarse grained processing on the NN interval sequence $\{x_1, \ldots, x_i, \ldots, x_N\}$ in step 2), to obtain reconstructed sequences $$y_j^\tau = 1/\tau \sum_{i=(j-1)\tau+1}^{j\tau} x_i,$$

$1 \leq j \leq N/\tau$ with different scales, $\tau$ as a scale factor;

ii. calculating a sample entropy $$S_E(m, r, N) = \ln \frac{\sum_{i=1}^{N-m} n_i'^m}{\sum_{i=1}^{N-m} n_i'^{m+1}}$$

for each scale's sequence $$y_j^\tau = 1/\tau \sum_{i=(j-1)\tau+1}^{j\tau} x_i.$$

iii. drawing a curve of the sample entropy with respect to the different scale factors, and obtaining characteristic parameters indicative of the heart rate complexity.

The characteristic parameters indicative of the heart rate complexity are acquired as follows:

For the curve in step iii, Slope n1 is obtained by linearly fitting points with scales of 1–n1; scales n2-n3 are segmented, and each area encompassed by each segment of the scale curve and the horizontal axis is calculated to obtain parameters Area1.

Further, n1<n2<n3, n3≤40; the number of parameters Area1 is between 1 and 7.

Further, n1=5, the slope parameter Slope is Slope 5, n2=6, n3=20. And parameters Area1 are Area1 1-5, Area1 6-15, and Area1 6-20.

Further, the selected sinus NN interval data is a NN interval data in an awake state.

Further, the selected sinus NN interval data is a 4-hour NN interval data in an awake state.

Further, the above-mentioned method is adaptable for vagus nerve-related diseases such as epilepsy or depression.

EMBODIMENTS

Example 1

Figure 1:
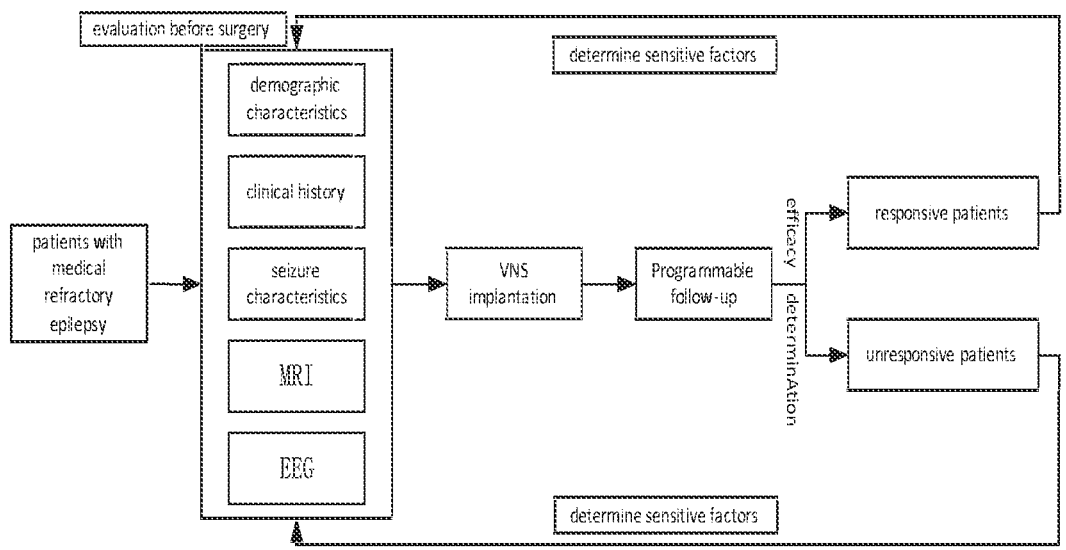
FIG. 1 is a flow chart of the prior art for screening patients with VNS indications.
Figure 2:
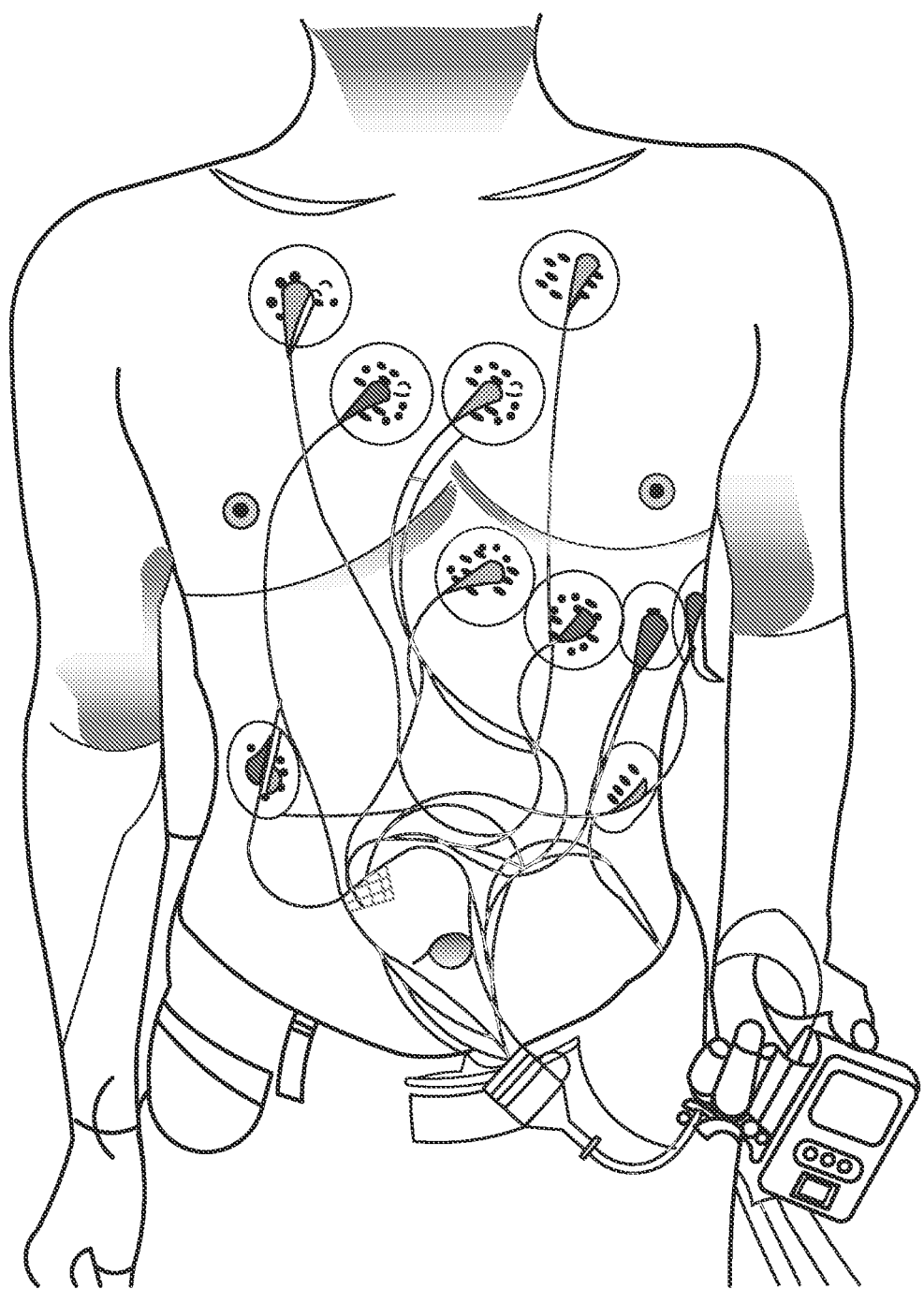
FIG. 2 is a diagram of 12-lead ECG acquisition.
Figure 3:
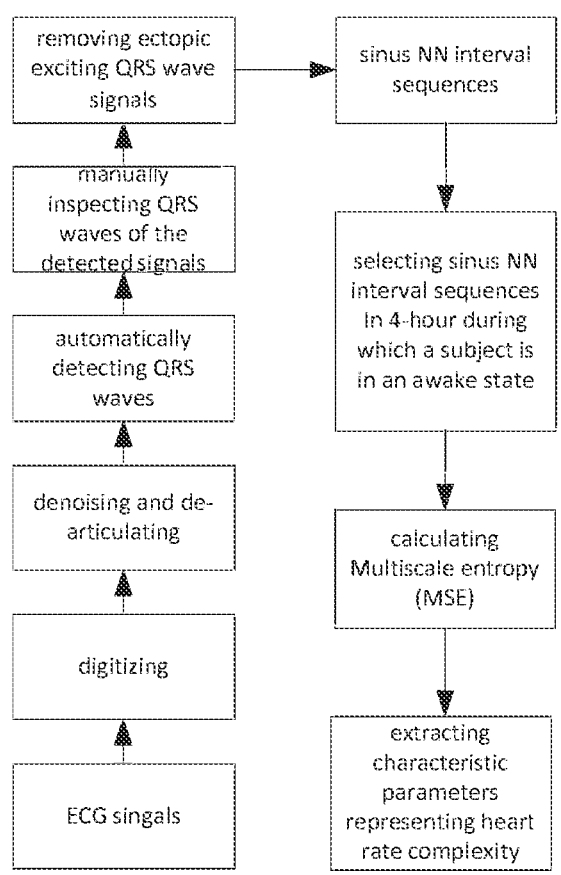
FIG. 3 is a flow chart of ECG signal processing.

As shown in FIG. 2, a standard 12-lead ECG acquisition for 24 hours before surgery requires: sampling frequency of the ECG acquisition device is greater than or equal to 500 Hz; during ECG recording, activities such as strenuous exercises and medications that could affect cardiac functions should be avoided; the recording period is 24 hours. Recording environment and conditions of subjects should be basically similar. The data used for HRV analysis should be ensured to be normal sinus NN intervals. During HRV analysis, normal sinus NN intervals of 4 hours are selected for MSE analysis from the 24-hour long-term ECG records during which the subject is in an awake state. The specific processing flow of ECG signals is shown in FIG. 3.

1) collecting and digitizing ECG signals;

2) denoising and de-articulating digital signals;

3) automatically detecting QRS waves thereof;

4) manually inspecting QRS waves of the detected signals;

5) removing ectopic exciting QRS wave signals;

6) forming a sinus NN interval sequence;

7) selecting 4-hour sinus NN interval sequences in the case of a subject in an awake state;

8) calculating MSE based on the 4-hour sinus NN interval sequences;

9) drawing a MSE curving, wherein the scale factor is as the horizontal and the entropy value corresponding to the scale factor is as the ordinate;

10) extracting characteristic parameters representing heart rate complexity, according to the MSE curve.

The MSE calculation method in the HRV analysis adopted in the present invention extracts characteristic parameters of Slope5, Area1-5, Area6-15, and Area6-20 to represent the heart rate complexity.

Figure 4:
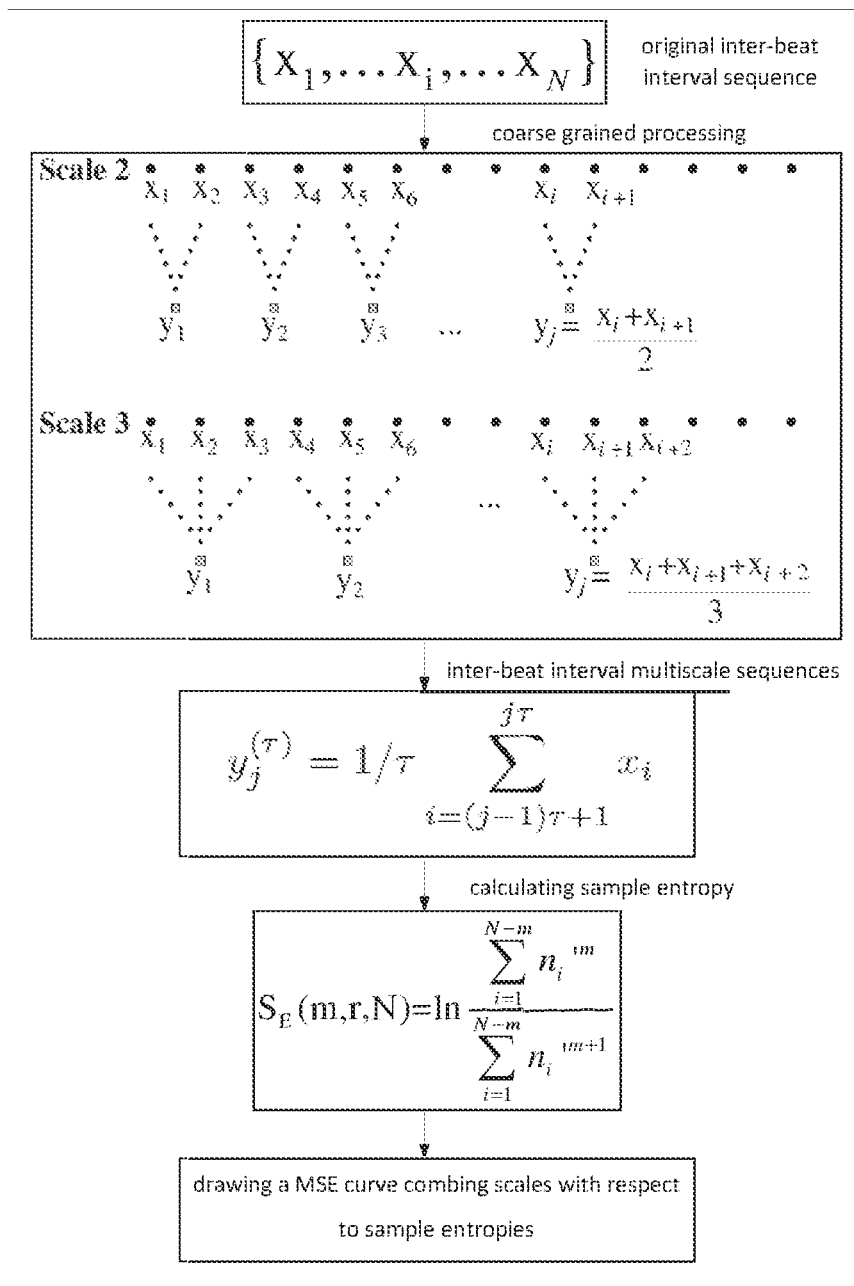
FIG. 4 is a flow chart of MSE analysis method.

The MSE method has the following steps (see FIG. 4):

(1) performing coarse grained processing on the 4-hour normal sinus NN interval sequence $\{x_1, \ldots, x_i, \ldots, x_N\}$, to obtain reconstructed sequences $$y_j^\tau = 1/\tau \sum_{i=(j-1)\tau+1}^{j\tau} x_i,$$

$1 \le j \le N/\tau$ with different scales, $\tau$ as a scale factor;

(2) calculating a sample entropy $$S_E(m, r, N) = \ln \frac{\sum_{i=1}^{N-m} n_i^{\prime m}}{\sum_{i=1}^{N-m} n_i^{\prime m+1}}$$

for each scale's sequence $$y_j^\tau = 1/\tau \sum_{i=(j-1)\tau+1}^{j\tau} x_i;$$

Figure 5:
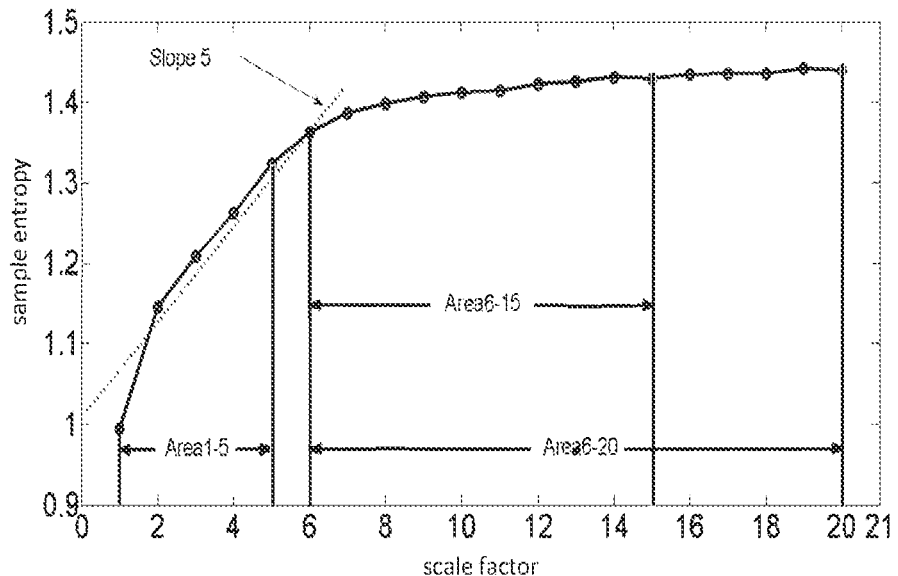
FIG. 5 is a diagram of extracting indicators of MSE Complexity.

(3) drawing a curve of the sample entropies with respect to the different scale factors, shown in FIG. 5; linearly fitting points of scales 1-5 to obtain slope 5; then calculating Area1-5, Area 6-15, and Area 6-20 encompassed by scale 1-5, scale 6-15, scale 6-20 curve and the horizontal axis, wherein, the above four parameters are characteristic parameters representing the heart rate complexity.

Figure 6:
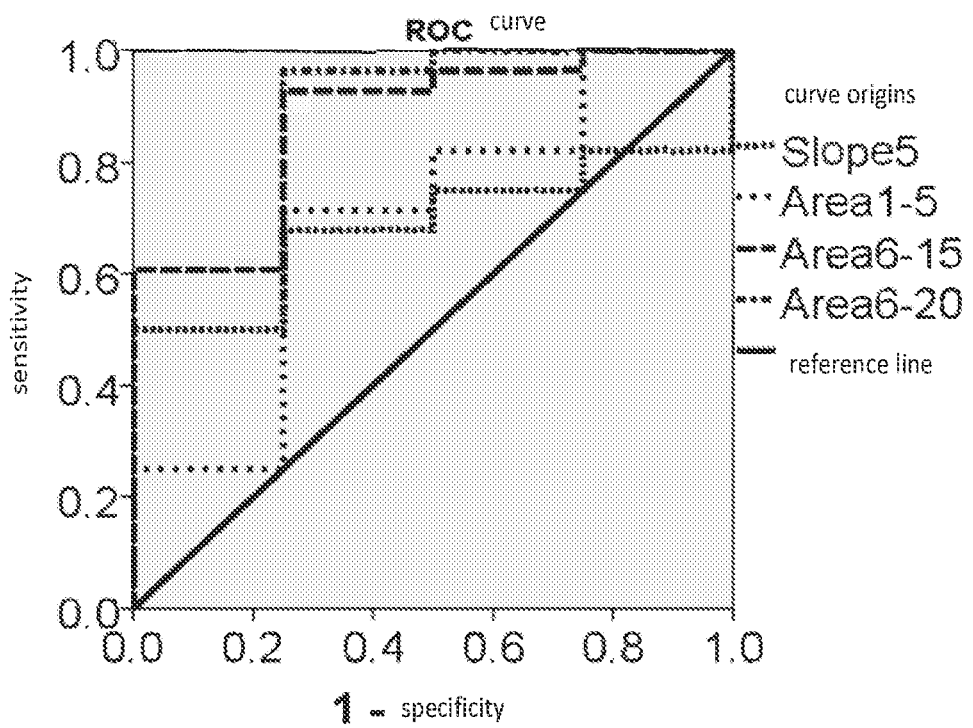
FIG. 6 is a threshold selection ROC curve
Figure 7:
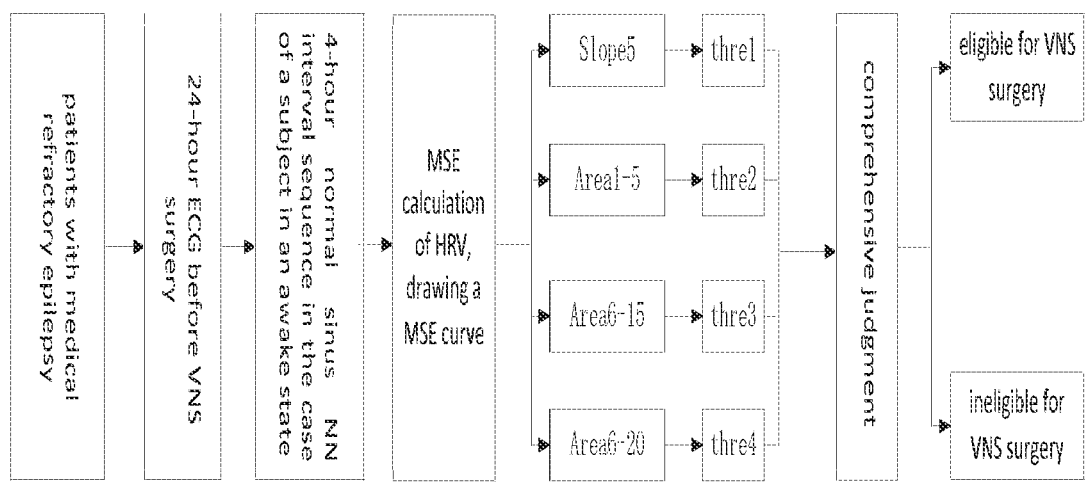
FIG. 7 is a flow chart for judgment.

For patients with drug-resistant epilepsy, 24-hour electrocardiogram acquisition was performed before surgery. The 24-hour electrocardiogram data collected was processed, according to the above-mentioned method, to obtain 4-hour normal sinus NN interval sequences during which the subject is in an awake state. The MSE analysis was performed on the above-mentioned 4-hour NN interval sequences according to the above-mentioned method. Characteristic parameters such as Slope5, Area1-5, Area6-15, Area6-20, etc., which represent heart rate complexity, were extracted. Then comprehensive judgment selection was performed through corresponding threshold judgment (as shown in FIG. 6). The VNS surgical patients in the training set were classified according to follow-up efficacy after a certain period of time (effective group and ineffective group). The above-mentioned heart rate complexity indicators of the effective group and the ineffective group were statistically analyzed, and Receiver Operating Characteristic (ROC) curves were drawn for Slope5, Area 1-5, Area 6-15, and Area 6-20. The threshold of each indicator (Youden index) is a point in each curve which has the shortest distance to the top left corner (that is, the coordinates (1, 1)). Finally, patients who are eligible for VNS surgery and patients who are not eligible for VNS surgery are distinguished based on the corresponding threshold (as shown in FIG. 7). When the four characteristic parameters Slope5, Area1-5, Area6-15 and Area6-20, representing heart rate complexity, are used to distinguish patients eligible for VNS surgery from patients ineligible for VNS surgery respectively, their corresponding threshold value selection and their corresponding screening accuracy are as follows:

When Slope5=0.071, patients with a value higher than said value were considered eligible for VNS surgery. The screening accuracy was 67.9%.

When Area 1-5=4.32, patients with a value higher than said value were considered eligible for VNS surgery. The screening accuracy was 71.4%.

When Area6-15=10.57, patients with a value higher than said value were considered eligible for VNS surgery. The screening accuracy was 92.9%.

When Area6-20=15.85, patients with a value higher than said value were considered eligible for VNS surgery. The screening accuracy was 96.4%.

Example 2

The complexity indicator Area 6-n, when the scale factor in the MES analysis method of Example 1 is expanded to n, could also be used for screening VNS patients as described above.

In the present invention, for patients with medical refractory epilepsy, 24-hours electrocardiogram acquisition before surgery and the MSE analysis of HRV were performed. In this way, patients with medical refractory epilepsy could be screened before surgery, thereby guiding patients who are not eligible for VNS therapy not to receive the surgery and to choose other therapies, which could save unnecessary expenditures and avoiding delaying the optimal timing for treatment. Meanwhile, patients with VNS surgical indications were clearly selected by extracting characteristic parameters representing heart rate complexity through ECG's MSE curve, which could improve overall VNS therapeutic efficacy.

Example 3

In accordance with the above screening method, 32 patients with medical refractory epilepsy, who had undergone VNS surgery at Beijing Tiantan Hospital from Aug. 13, 2014 to Dec. 31, 2014, were selected for test. Before VNS surgery, these 32 patients with medical refractory epilepsy were comprehensively evaluated (including demographic characteristics, clinical history, history of antiepileptic medication, 24-hours video-EEG, MRI, and 24-hour dynamic electrocardiogram etc.).

According to the above ECG signal processing method, the MSE analysis was performed, based on 24-hour dynamic electrocardiographic data. The corresponding characteristic parameters Slope5, Area1-5, Area6-15, and Area6-20 were extracted based on each patient's MSE curve. At the end of 1-year follow-up, among 32 patients with medical refractory epilepsy who had undergone VNS treatment, 28 patients' seizure frequencies had been reduced to various degrees (seizures had been completely controlled in 6 patients), who were considered as the effective group, and the remaining 4 patients' seizure frequencies after VNS surgery hadn't changed compared with those before VNS surgery, who were considered as the ineffective group. The MSE curves of the effective group and the ineffective group differ greatly, which suggested that the MSE method could be adapted to screen patients with VNS indications. Furthermore, each patient's characteristic parameters Slope5, Area1-5, Area6-15, and Area6-20 before surgery could be adapted to predict efficacy. The results shown that, among the above four parameters, Area6-20 was the most accurate parameter: when its threshold was set to 15.85, only one patient's Area6-20 was 15.09 among the 28 effective patients, as shown in Table 1, and the rest patients' Area6-20 were greater than 15.85. The screening accuracy rate exceeded 96%, which confirmed that the MSE method of the above HRV analysis could accurately and effectively screen patients with VNS indications.

TABLE 1

|  |  | Slope5 | Area1-5 | Area6-15 | Area6-20 |
|---|---|---|---|---|---|
| Effective group | patient1 | 0.141 | 5.651 | 14.074 | 21.871 |
|  | patient2 | 0.098 | 2.925 | 9.587 | 15.093 |
|  | patient3 | 0.012 | 7.596 | 16.155 | 24.702 |
|  | patient4 | 0.069 | 5.341 | 14.477 | 23.084 |
|  | patient5 | 0.081 | 4.531 | 10.915 | 17.081 |
|  | patient6 | 0.045 | 6.766 | 16.296 | 25.248 |
|  | patient7 | 0.092 | 4.150 | 11.503 | 18.059 |
|  | patient8 | 0.101 | 3.685 | 11.804 | 18.769 |
|  | patient9 | 0.091 | 6.962 | 17.257 | 27.045 |
|  | patient10 | 0.177 | 3.983 | 14.009 | 22.139 |
|  | patient11 | 0.169 | 5.571 | 14.666 | 23.090 |
|  | patient12 | 0.116 | 5.529 | 15.255 | 23.922 |
|  | patient13 | 0.112 | 4.124 | 11.135 | 17.381 |
|  | patient14 | 0.144 | 4.189 | 12.097 | 19.044 |
|  | patient15 | 0.099 | 4.953 | 12.932 | 20.050 |
|  | patient16 | 0.070 | 5.904 | 13.657 | 21.414 |
|  | patient17 | 0.172 | 4.599 | 11.162 | 16.557 |
|  | patient18 | -0.024 | 5.839 | 13.736 | 21.497 |
|  | patient19 | 0.098 | 6.115 | 15.443 | 23.849 |
|  | patient20 | -0.066 | 5.197 | 11.964 | 19.043 |
|  | patient21 | 0.072 | 3.875 | 10.273 | 16.025 |
|  | patient22 | 0.087 | 5.132 | 14.689 | 23.120 |
|  | patient23 | 0.101 | 6.058 | 15.677 | 24.371 |
|  | patient24 | 0.053 | 4.871 | 14.701 | 23.563 |
|  | patient25 | 0.128 | 5.580 | 15.252 | 23.891 |
|  | patient26 | -0.041 | 5.299 | 13.201 | 20.832 |
|  | patient27 | 0.107 | 4.417 | 13.854 | 21.959 |
|  | patient28 | 0.030 | 3.322 | 10.847 | 17.468 |
| Ineffective group | patient29 | 0.070 | 4.226 | 9.647 | 14.219 |
|  | patient30 | 0.093 | 5.740 | 12.949 | 20.118 |
|  | patient31 | 0.033 | 2.257 | 7.488 | 12.139 |
|  | patient32 | 0.068 | 4.043 | 10.298 | 15.680 |

The above description is only preferred embodiments of the present invention. It should be noted that, those skilled in the art can make improvements and modifications, without departing from the principle of the present invention. These improvements and modifications should be regarded in the scope of the present invention. In addition, although specific terms are used in this description, these terms are merely for convenience of illustration and do not constitute any limitation to the present invention.

The invention claimed is:

1. A method for screening surgical patients with Vagus Nerve Stimulation (VNS) indications, wherein the method comprises:
   collecting electrocardiography (ECG) data in vitro from patients with vagus nerve-related diseases;
   selecting sinus normal-to-normal (NN) interval data using the ECG data;
   performing a multiscale entropy (MSE) calculation on the selected sinus normal-to-normal (NN) interval data, wherein performing the MSE calculation comprises:
      performing coarse grained processing on the normal-to-normal (NN) interval data $\{x_1, \ldots, x_i, \ldots, x_N\}$, to obtain reconstructed sequences using an equation $$y_j^\tau = 1/\tau \sum_{i=(j-1)\tau+1}^{j\tau} x_i,$$

$1 \leq j \leq N/\tau$, where $\tau$ is a given scale factor, $\tau=1, 2, 3, \ldots q$;
      calculating a sample entropy for each reconstructed sequence with a different scale factor $\tau$; and
      drawing a MSE curve of the sample entropy with respect to the different scale factors with the scale factor as a horizontal axis and the sample entropy as a vertical axis;
   extracting parameters representing heart rate complexity using the MSE curve, wherein extracting the parameters representing heart rate complexity further includes:
      for the MSE curve and the different scale factors including scale n1, scale n2, and scale n3, wherein scale n1<scale n2<scale n3, obtaining at least slope n1 by linearly fitting points of the curve that corresponds with the scale 1 to scale n1, wherein scale n3<40;
      dividing the curve from the scale n2 to the scale n3 into a plurality of segments; and
      calculating area parameters for each area encompassed by each segment of the plurality of segments of the curve to obtain the parameters representing heart rate complexity;
   setting thresholds for the parameters representing heart rate complexity, the thresholds indicating patients who are suitable for VNS implantation surgery and those who are not suitable for VNS implantation surgery;
   constructing a model for patients with vagus nerve-related diseases based on heart rate variability as represented by the extracted parameters and the thresholds; and
   identifying patients who are suitable for VNS implantation surgery using the model;
   providing the VNS implantation surgery to the identified patients.

2. The method of claim 1, wherein scale n1=5, the slope parameter Slope is Slope5, scale n2=6, scale n3=20, and Area parameters are Area 1-5, Area 6-15, and Area 6-20.

3. The method of claim 1, wherein the selected sinus normal-to-normal (NN) interval data is normal-to-normal (NN) interval data in an awake state.

4. The method of claim 3, wherein the selected sinus normal-to-normal (NN) interval data is normal-to-normal (NN) interval data collected within 4 hours in an awake state.

5. A method for screening surgical patients with Vagus Nerve Stimulation (VNS) indications, wherein the method comprises:
   collecting electrocardiography (ECG) data in vitro from patients with vagus nerve-related diseases;
   selecting sinus normal-to-normal (NN) interval data using the ECG data;
   performing a multiscale entropy (MSE) calculation on the selected sinus normal-to-normal (NN) interval data, wherein performing the MSE calculation comprises:

performing coarse grained processing on the normal-to-normal (NN) interval data $\{x_1, \ldots, x_i, \ldots, x_N\}$, to obtain reconstructed sequences using an equation $$y_j^\tau = 1/\tau \sum_{i=(j-1)\tau+1}^{j\tau} x_i.$$

$1 \leq j \leq N/\tau$, where $\tau$ is a given scale factor, $\tau = 1, 2, 3, \ldots q$;

calculating a sample entropy for each reconstructed sequence with a different scale factor $\tau$; and drawing a MSE curve of the sample entropy with respect to the different scale factors with the scale factor as a horizontal axis and the sample entropy as a vertical axis;

extracting parameters representing heart rate complexity using the MSE curve, wherein extracting the parameters representing heart rate complexity further includes:

for the MSE curve and the different scale factors including scale n1, scale n2, and scale n3, wherein scale n1<scale n2<scale n3, obtaining at least slope n1 by linearly fitting points of the curve that corresponds with the scale 1 to scale n1;

dividing the curve from the scale n2 to the scale n3 into a plurality of segments; and calculating area parameters for each area encompassed by each segment of the plurality of segments of the curve to obtain the parameters representing heart rate complexity;

setting thresholds for the parameters representing heart rate complexity, the thresholds indicating patients who are suitable for VNS implantation surgery and those who are not suitable for VNS implantation surgery;

constructing a model for patients with vagus nerve-related diseases based on heart rate variability as represented by the extracted parameters and the thresholds; and identifying patients who are suitable for VNS implantation surgery using the model;

wherein scale n1=5, the slope parameter Slope is Slope5, scale n2=6, scale n3=20, and Area parameters are Area 1-5, Area 6-15, and Area 6-20;

providing the VNS implantation surgery to the identified patients.

\* \* \* \* \*